(12) United States Patent
Christians et al.

(10) Patent No.: US 6,372,756 B1
(45) Date of Patent: Apr. 16, 2002

(54) EPIMORPHIAN COMPOUND AND ITS USE

(75) Inventors: Uwe Christians, San Rafael, CA (US); Volkhard W. Kaever, Burgdorf (DE)

(73) Assignee: AvMax, Inc., South San Francisco, CA (US)

( * ) Notice: Subject to any disclaimer, the term of this patent is extended or adjusted under 35 U.S.C. 154(b) by 0 days.

(21) Appl. No.: 09/252,549

(22) Filed: Feb. 19, 1999

Related U.S. Application Data

(60) Provisional application No. 60/075,469, filed on Feb. 20, 1998.
(51) Int. Cl.[7] ............... A61K 31/444; A61K 31/44; C07D 221/18; C07D 221/22
(52) U.S. Cl. ............... 514/289; 546/74; 546/75
(58) Field of Search ............... 514/289; 546/74, 546/75

(56) References Cited

PUBLICATIONS

Hitotsuyangi, Y., et al., "Syntheses of Antitumor Morphinane alkaloids, Sinococuline and 6–epi–, 7–epi, and 6–epi–7–epi–Sinococuline, from Sinomenine," *J. Org. Chem.*, 60(14):4549–4558 (1995).

Candinas, D., et al., Immunomodulatory Effects of the Alkaloid Sinomenine in the High Responder ACI–to–Lewis Cardiac Allograft Model, *Transplantation*, 62(12):1855–1860 (1996).

Chen–ling, Zhu, Clinical Studies of Sinomenium Acutum on 311 Rheumatoid Arthritis Cases, *Bulletin of Chinese Medicinal Herbs*, 11:41–44 (1979).

Hojo, H., et al., Effect of Sinomenine on Antibody Responses in Mice, *J. of Immunopharmac.*, 7(1):33–42 (1985).

Junbao, L., et al., Pharmacokinetic Parameters and Bioavailability of Sinomenine Hydrochloride, *J. Xi'an Med. Univ.*, 4(1):16–19 (1992).

Kaever, V., et al., Immunomodulatory Properties of the Anti–Arthritic Alkaloid Sinomenine, 9th International Congress of Immunology, Abstract (1995).

Kametani, T., et al., Studies on the Syntheses of Heterocyclic Compounds. Part CCC. Syntheses of Salutaridine, Sinoacutine, and Thebaine. Formal Total Syntheses of Morphine and Sinomenine, *J. Chem. Soc.*, (C)2030–2033 (1969).

Kondo, Y., et al., Protection by Sinomenine Against Endotoxin–Induced Fulminant Hepatitis in Galactosamine–Sensitized Mice, *Biochem. Pharma.*, 48(5): 1050–1052 (1994).

Liu, L., et al., Inhibition of Lymphocyte Proliferation by the Anti–Arthritic Drug Sinomenine, *Int. J. Immunopharmac.*, 16(8):685–691 (1994).

Liu, L., et al., Impairment of Macrophage Eicosanoid and Nitric Oxide Production by an Alkaloid from Sinomenium Acutum, *Arzneimittel–Forschung/Drug Research*, 44(II), 11:1223–1226 (1994).

Liu, L. et al, Amelioration of Rat Experimental Arthritides by Treatment with the Alkaloid Sinomenine, *Int. J. Immunopharmac.*, 18(10):529–543 (1996).

Nozaka, T., et al., Mutagenicity of Isoquinoline Alkaloids, Especially of the Aporphine Type, *Mutation Res.*, 240:267–279 (1990).

(List continued on next page.)

*Primary Examiner*—Alan L. Rotman
(74) *Attorney, Agent, or Firm*—Cooley Godward LLP

(57) ABSTRACT

A novel compound N-demethyl-sinomenine, a metabolite of the anti-arthritic alkaloid sinomenine, has been identified and characterized. The compound may be incorporated in a pharmaceutical composition and may be administered to patients for treatment of various disorders, such as rheumatoid arthritis. The novel compound has superior biological activity and water solubility as compared to sinomenine.

18 Claims, 12 Drawing Sheets

OTHER PUBLICATIONS

Okuda, T., et al., A Case of Drug Eruption Caused by the Crude Drug Boi® (Sinomenium Stem/Sinomeni Caulis et Rhizoma), *J. Derma.*, 22:795–800 (1995).

Pu–mine, S., et al., Treatment of Rheumatoid Arthritis with Sinomenine on 60 Cases, J. Xien Yi Xue, 10(9):292 (1985).

Shiao–yin, K., et al., Clinical Trials of Sinomenine on the Treatment of Rheumatoid Arthritis, *J. Beijing Med.*, 8(3):186–189 (1986).

Wheeler, D.M.S., et al., Mass Spectral Studies of Alkaloids Related to Morphine, *J. Am. Chem. Soc.*, 89(17):4494–4501 (1967).

Yamasaki, H., Pharmacology of Sinomenine, an Anti–Rheumatic Alkaloid From Sinomenium Acutum, *Acta Med., Okayama*, 30:1–20 (1976).

$C_{18}H_{21}NO_4$
MW 315

$C_{19}H_{23}NO_4$
NW 329

EPIMORPHIAN COMPOUND AND ITS USE

CROSS REFERENCE TO RELATED APPLICATION

This application claims the benefit of U.S. application No. 60/075,469, filed of Feb. 20, 1998.

TECHNICAL FIELD

The present invention relates to a novel chemical compound useful as an analgesic, anti-inflammatory, and immunosuppressive compound when administered to patients.

BACKGROUND

Sinomenine, which has a molecular formula of $C_{19}H_{23}NO_4$, is a crystalline alkaloid derived from a medicinal plant, Sinomenium acutum. Sinomenine has long been used in China and Japan as a drug of Kampo traditional medicine for the treatment of neuralgia and rheumatic diseases, and has also been a popular example of an opiate useful for mass spectrometry studies conducted in the 1960s in the United States and elsewhere.

Sinomenine has been used for the treatment of various diseases and ailments (Wong, K.C., et al., *History of Chinese Medicine*, National Quarantine Service, Shanghi, 2nd ed., pp. 119, (1936)), including pain, inflammation, cough, and autoimmune or chronic inflammatory diseases such as rheumatoid arthritis. Sinomenine exerts moderate analgesic and potent anti-inflammatory (Huo, H. R., et al., *Study on the Mechanism of Sinomenine on Analgesic and Anti-Inflammatory Activities, Xi'an Yike Daxue Xuebao*, 10:346–349, (1989)) and immunosuppressive properties (Hojo, H., et al., *Effect of Sinomenine on Antibody Responses in Mice, J. Immunopharmocol*, 7:33–42, (1985); Liu, L., et al., *Inhibition of Lymphocyte Proliferation by the Anti-Arthritic Drug Sinomenine, Int. J. Immunopharmocol*, 16:685–691, (1994)). Sinomenine has also been shown to have immunomodulatory properties (Kaever, V. et al., *Immunomodulatory Properties of the Anti-Arthritic Alkaloid Sinomenine*, Abstract: 9th International Congress of Immunology (1995). Further, there is evidence of sinomenine having histamine-releasing properties (Okayama 1976). Additionally, animal studies have shown a protective effect against fulminant hepatitis (Kondo, Y., et al., *Protection by Sinomenine Against Endotoxin-Induced Fulminant Hepatitis in Galactosamine-Sensitized Mice, Biochem. Pharmacol.*, 48:1050–1052, (1994)) and effectiveness in reversal of cardiac arrythmias (Sun, F., et al., *The Effect of Sinomenine on Experimental Arrythmia, Xi'an Yike Daxue Xuebao*, 11:324–326, (1990)). The efficacy of sinomenine in the therapy of rheumatic arthritis has been confirmed by clinical studies (Key, S. Y., et al., *Clinical Trials of Sinomenine on the Treatment of Rheumatoid Arthritis, Beijing Yi Xue*, 8:183–186, (1986)).

Additionally, the immunosuppressive effects of sinomenine on lymphocytes and macrophages in vitro have previously been examined (Liu, L. et al., *Inhibition of Lymphocyte Proliferation by the Anti-Arthritic Drug Sinomenine, Int. J. Immunopharmac.*, 16(8):685–691 (1994)). Lymphocyte proliferation, which likely plays a key role in rheumatic disease (Panayi, G. S., *The Immunopathogenesis of Rheumatoid Arthritis, Br. J. Rheumat.*, 32 (suppl. 1):4–14, (1993)), can be inhibited by sinomenine in a reversible manner without exhibiting direct cytotoxic effects (Hojo, H., et al., *Effect of Sinomenine on Antibody Responses in Mice, J. Immunopharmacol*, 7(1):33–42, (1985); Liu, L. et al., *Inhibition of Lymphocyte Proliferation by the Anti-Arthritic Drug Sinomenine, Int. J. Immunopharmac.*, 16(8):685–691 (1994); Liu, L., et al., *Impairment of Macrophage Eicosanoid and Nitric Oxide Production by an Alkaloid Extracted From Sinomenine Acutum, Arzneim-Forschung/Drug Res.*, 44:1223–1226, (1994)). The molecular mechanisms underlying its inhibitory effect on T-lymphocyte proliferation are still unclear but the involvement of opioid receptors in T-lymphocyctes is likely (Wybran, J., et al., *Suggestive Evidence for Receptors for Morphine and Methionine-Enkephaline on Normal Blood T-Lymphocytes, J. Immunol.*, 123:1068–1070, (1979)).

Typically, sinomenine is extracted from the dried plant *Sinomenium acutum*. There is evidence that it has been administered subcutaneously and orally as a decoction of the roots and stems of *Sinomenium acutum*. For a less crude extract, the stems of the dried plant are soaked in 10% azua ammoniae and homogenized. The homogenate is soaked in benzol for one week, then 2% HCl is added to the benzol solution and the entire homogenate is filtered. The extract is then alkalized with ammonium and a phase separation is performed with chloroform. The chloroform layer is selected and filtered again. The product is then dehydrated using anhydrous potassium carbonate and evaporated to dryness. The resulting crystals are further purified by a diethyl ether extraction.

Discovery of other, superior compounds for treatment would be advantageous since sinomenine finds wide use for the treatment of various medical conditions.

SUMMARY OF THE INVENTION

A novel compound, N-demethyl-sinomenine, also known as des-17-methyl-sinomenine, has been discovered and characterized. Thus, one aspect of the invention is a novel chemical compound, N-demethyl-sinomenine, or a pharmaceutically acceptable salt, ester, or hydrate form thereof. Another aspect of the invention is a pharmaceutical composition employing N-demethyl-sinomenine along with a pharmaceutically acceptable carrier. A further aspect of the invention is a method of treating a patient for a disorder by administration of N-demethyl-sinomenine to the patient.

Evidence is provided which indicates that the N-demethyl-sinomenine has an immnosuppressive activity as much as five-fold higher than sinomenine. N-demethyl-sinomenine also has a greater water solubility than sinomenine. Thus, this more potent compound may be administered in lieu of sinomenine, potentially lowering costs and increasing overall effectiveness.

DESCRIPTION OF SPECIFIC EMBODIMENTS

Figure 1:
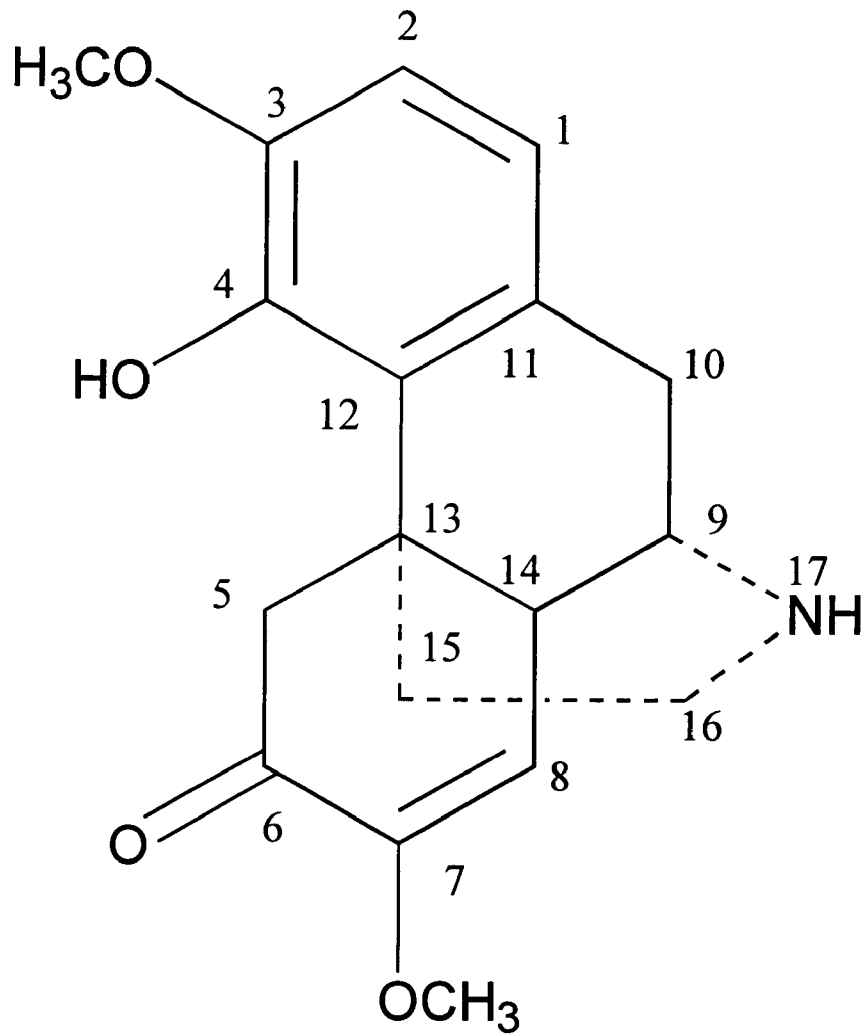
FIG. 1 represents the chemical structure of N-demethyl-sinomenine.

The novel compound N-demethyl-sinomenine, alternatively des-17-methyl-sinomenine, has a structure as shown in FIG. 1. The molecular formula of N-demethyl-sinomenine is $C_{18}H_{21}NO_4$ and the molecular weight is approximately 315 Daltons. N-demethyl-sinomenine is an epimorphian alkaloid with a four ring structure.

The structure of N-demethyl-sinomenine differs from sinomenine (FIG. 2) by the lack of a methyl group at the 17-position. Surprisingly, the novel compound is biologically more active than sinomenine. In fact, N-demethyl-sinomenine shows approximately five times the immunosuppressive activity of sinomenine. Thus, the high potency N-demethyl-sinomenine may be administered to patients in smaller amounts, potentially lowering costs and improving effectiveness as compared to the administration of sinomenine.

Another difference between N-demethyl-sinomenine and sinomenine is the superior water solubility of N-demethyl-sinomenine. This characteristic of the novel compound results in a different oral bioavailability, pharmacokinetic profile, and organ distribution pattern than the known compound and also leads to ease in creating formulations for therapeutic use. The greater water solubility of the N-demethyl-sinomenine over sinomenine is evidenced by the shorter retention time of N-demethyl-sinomenine on a lipophilic reversed-phase HPLC column.

N-demethyl-sinomenine is a major metabolite of sinomenine, believed to represent approximately 90% of all sinomenine metabolic products. It has never before been isolated and purified nor characterized and prepared for combination with a pharmaceutically acceptable carrier. As used herein, "major metabolite" of sinomenine refers to N-demethyl sinomenine.

N-demethyl-sinomenine may be produced by treatment of liver microsomes with sinomenine and a nicotinamide adenine dinucleotide phosphate (NADPH) generating system. Production of N-demethyl-sinomenine on a larger scale may be effected in several different manners, several examples of which are described below. Purification of the N-demethyl-sinomenine may be done by the method presented in Example 1, on a larger scale if necessary, or by another method of purification known in the art. The sinomenine starting material needed for some of the procedures described may be obtained from a commercial supplier (e.g., Aldrich, Milwaukee, Wis.) or may be prepared according to traditional Chinese methods.

According to one method, modification of sinomenine starting material may be performed by modified cells or microorganisms. Specifically, bacteria or insect cells in which specific cytochrome P450 enzymes are overexpressed are commercially available (e.g., Gentest, Woburn, Mass.). Sinomenine may be allowed to react in one of these systems, followed by extraction and purification using large-scale preparative chromatographic procedures. Organisms which naturally express cytochrome P450 or enzymes with cytochrome P450-like activity, such as bacteria, actinomyces, or fungi, may also be used. For example, see Kuhnt, M., et al., *Microbial conversion of rapamycin*, Enzyme and Microbial Technology 21:405–412 (1997); Chen, T. S., et al., *Microbial transformation of immunosuppressive compounds. 1. Desmethylation of FK506 and immunomycin (FR 900520) by Actinoplanes sp. ATCC 53771*, J.Antibiot., 45:118–123 (1992); and Chen, T. S., et al., *Microbial transformation of immunosuppressive compounds. II. Specific desmethylation of 13-methoxy group of FK506 and immunomycin (FR 900520) by Actinoplanes sp. ATCC 53828*, J.Antibiot., 45:577–580 (1992);

Another method of producing N-demethyl-sinomenine is via chemical N-demethylation of sinomenine. For example, N-demethylation by photo-sensitized oxygenation may be performed to produce norcodein from codein (Lindner, J., et al., *Demethylation of codein to norcodein by sensitized photo-oxygenation*, Tetrahedron Letters 17:1705–1706 (1972)). Thus, building on the procedures described by Lindner et al., sinomenine may be incubated in five parts 2,5-dimethyl furan to one part water (v/v) with Bengalrosa at 20° C. in the presence of light ($3.3 \times 10^{-2}$ m wavelength) and oxygen. After addition of sulfuric acid and elimination of Bengalrosa by filtration, the N-demethylated product may be purified by column chromatography.

N-demethyl-sinomenine may be also be obtained through total synthesis, e.g. by adaptation of the procedures described by Kametani et al., (Kametani, T., et al., *Studies on the synthesis of heterocyclic compounds. Part ccc. Synthesis of salutridine, sinoacutine, and thebaine. Formal total syntheses of morphine and sinomenine.*, J. Chem. Soc. (C), 15:2030–2033 (1969)). Specifically, total synthesis begins with diazotization of (±) 1-(2-amino-3-benzyloxy-4-methoxybenzyl)-1,2,3,4,-tetrahydro-6,7-dimethoxy-2-methylisoquinoline, followed by the thermal decomposition of the resulting diazonium salt. The result would be (±) salutaridine which is converted into (±) thebaine by incubation of (±) salutaridine with methanol and sodium borohydride. After incubation at 0° C. for 1 hour, evaporation of methanol, and extraction with 10% aqueous ammonium chloride and chloroform, the resulting intermediate, a mixture of epimeric alcohols, is treated with N-hydrochloric acid for 1 hour. From this solution (±) thebaine is isolated by liquid-liquid extraction (addition of 10% sodium hydroxide and extraction into chloroform) and a solid liquid purification step using preparative thick-layer chromatography on a silica gel. (±) N-demethyl sinomenine is then synthesized from (±) thebaine using a modification of the procedure of Okabe K., et al., *Jap. J. Pharm. Chem.* 39:267 (1968). As an alternative to total synthesis, the intermediate products (±) salutaridine or (±) thebaine could be used as starters for N-demethyl-sinomenine synthesis.

The compound of the invention encompasses not just N-demethyl-sinomenine as shown in FIG. 1, but also pharmaceutically acceptable salts, esters, or hydrates thereof. "Pharmaceutically-acceptable salt or ester" means a salt or ester that retains the biological effectiveness and properties of N-demethyl-sinomenine, and that is not biologically or otherwise undesirable. N-demethyl-sinomenine is capable of forming both acid and base salts by virtue of the presence of phenolic and amino groups and is capable of forming esters by virtue of the phenolic group. Additionally, a hydrate form of the compound can be created by virtue of the amino group. Pharmaceutically-acceptable base addition salts include, but are not limited to, the sodium, potassium, lithium, ammonium, calcium, and magnesium salts. Pharmaceutically-acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically-acceptable esters include esters of alkanoic, alkenoic, alkynoic and benzoic or other aromatic acids.

For example, the novel compound may be more generally represented as follows:

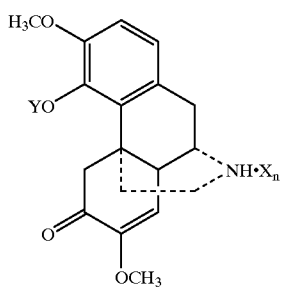

wherein there is an optional substitution at $X_n$ to make a pharmaceutically acceptable salt or hydrate of the compound and further wherein Y is hydrogen or there is a substitution at Y to make a pharmaceutically acceptable salt or ester of the compound. In other words, the compound could have, at position 17, NH alone, or substitutions to make a salt or hydrate form of the compound. The X is preferably $H_2O$ or is selected from the list of pharmaceutically acceptable acid addition salts. Y is H or is preferably selected from the list of pharmaceutically acceptable base addition salts. Alternatively, there is a substitution of the YO group to make a pharmaceutically acceptable ester.

More specifically, a pharmaceutically acceptable salt or hydrate of the compound can be made by a substitution at $X_n$ wherein n is a number from 1–5 and X is $H_2O$ or is derived from the group consisting of hydrochloric acid, hydrobromic acid, sulfuric acid, nitric acid, phosphoric acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. A pharmaceutically acceptable salt of the compound can be made by a substitution at Y wherein Y is selected from the group consisting of sodium, potassium, lithium, ammonium, calcium, or magnesium. A pharmaceutically acceptable ester of the compound can be made by a substitution at YO wherein YO is selected from the group consisting of esters of alkanoic acids, alkenoic acids, alkynoic acids, and benzoic or other aromatic acids.

In addition to including the novel compound N-demethyl-sinomenine, which may be used for research or therapeutic purposes, the invention includes a pharmaceutical composition. N-demethyl-sinomenine is particularly useful when combined with a pharmaceutically acceptable carrier, and indeed another aspect of the invention is a pharmaceutical composition comprising N-demethyl-sinomenine and a pharmaceutically acceptable carrier. For example, the compound may be reconstituted in saline or water for administration to a patient parenterally. Other dosage forms may also be used such as tablet, capsule, or drinking solution. The compound may be administered orally, topically, or injected intravenously, subcutaneously, or intramuscularly. The carrier will be one that is readily mixed with the N-demethyl-sinomenine to form a composition that is administrable by parenteral or oral means. Thus, the carrier is preferably water, which may have other pharmaceutically acceptable excipients included to ensure its suitability for administration. The resulting composition should be sterile if administered parenterally and should also have acceptable osmotic properties. In general, a suitable parenteral formulation is prepared in accordance with standard techniques known to one of skill in the art.

Another aspect of the invention is a method of treating a patient, especially a human patient, for a disorder by administering N-demethyl-sinomenine to the patient. N-demethyl-sinomenine is useful as an immunosuppressive, anti-inflammatory, or analgesic agent. The N-demethyl-sinomenine may be given to a patient for treatment of disorders where sinomenine is indicated and may be useful for treatment of further disorders. For example, the N-demethyl-sinomenine is useful in the treatment of rheumatic diseases, such as rheumatoid arthritis, neuralgia, ankylosing spondylitis, Reiter's syndrome, and Behcet's syndrome, and in autoimmune diseases such as lupus erythematosus and certain types of nephritis or psoriasis. Further, it may be used for the treatment of multiple sclerosis, hepatitis, vasculitis, and diseases involving inflammatory degeneration such as atherosclerosis or bronchiolitis obliterans. The pharmaceutical composition may also find use in transplantation medicine to prevent the rejection of transplanted organs or cells, as may occur with allogeneic transplants or xenotransplants. The N-demethyl-sinomenine may be used alone or in combination with other immunosuppressive, anti-inflammatory, or analgesic drugs.

The term "treatment" as used herein includes administration to a mammal, particularly a human, for the following purposes: (i) preventing the disease from occurring in a subject which may be predisposed to the disease but has not yet been diagnosed as having it; (ii) inhibiting the disease, i.e. arresting its development; or (iii) relieving the disease, i.e. causing regression of the disease.

Traditionally, sinomenine has been administered subcutaneously or orally as a decoction of the roots and stems of *Sinomenium acutum*. The usual dosage for injections is reported as 20 mg once daily with an increase of 10–15 mg every 3–4 days up to a maximum daily dose of 90–100 mg. For oral administration, the recommended intake has been reported as being anywhere from 30–120 mg/day in three divided doses (Yamasaki, H., *Pharmacology of sinomenine, an Anti-Rheumatic Alkaloid from Sinomenium Acutum, Acta Med. Okayama*, 30:1–20 (1976)) to 180–300 mg/day in three divided doses (Shi, P. et al., *Treatment of Rheumatoid Arthritis with Sinomenine on 60 Cases, J. Xien Yi Xue*, 10(9):292 (1985)). Because the N-demethyl-sinomenine is more potent than sinomenine, administration of a smaller amount of N-demethyl-sinomenine as compared to sinomenine is generally warranted to minimize the potential for side effects. Sinomenine sometimes causes minor side effects such as mild pain, cough, and diarrhea. Typical side effects associated generally with immunosuppression include increased incidence of bacterial, fungal and/or viral infections. In instances of long-term use of immunosuppressive agents, there may be an increased risk of cancer.

The invention being fully described, reference will be made to the following non-limiting examples.

EXAMPLES

Example 1
Small-Scale Preparation of N-Demethyl-Sinomenine

Sinomenine was incubated with either rat or human liver microsomes and an NADPH generating system. The compounds generated were purified using high performance liquid chromatography (HPLC), specifically reversed-phase HPLC. One major metabolite was isolated.

The livers of male Sprague Dawley rats, treated with dexamethasone for two days, and human liver specimens provided the sources for the starting material. Liver microsomes were prepared using standard centrifugation techniques as described by Guengerich (Guengerich, F. P., et al., *Microsomal Enzymes Involved in Toxicology-Analysis and Separation*, In: *Principles and Methods in Toxicology* (Ed. Hayes A W), pp. 609–637, Raven Press, New York, (1982)) with some modifications. Specifically, phosphate buffer was used instead of TRIS buffer and microsomes were stored at −80° C. The protein concentration was determined using a bicinchoninic acid assay (Redingbaugh, M. G., et al., *Adaptation of the Bicinchoninic Acit Protein Assay for Use With Microtiter Plates and Sucrose Gradient Fractions*, Anal. Biochem., 153:267–271, (1986)) and adjusted with 0.1 M potassium phosphate buffer, pH 7.4, to 3 g/l.

An NADPH generating solution was prepared by combining 6 mM EDTA (ethylene diaamine tetraacetate), 30 mM $MgCl_2+6 H_2O$, 2.5 mM NADP (Boehringer Mannheim, Mannheim, Germany), 54 mM isocitrate, and 700 U/l isocitrate dehydrogenase in 0.1 mM potassium phosphate buffer, pH 7.4. Isocitrate dehydrogenase uses isocitrate as a substrate and NADP as a co-factor, converting the NADP to NADPH. The NADPH is used, in turn, as a co-factor by cytochrome P450 enzymes.

After preparation of the microsomes and the NADPH generating solution, metabolites were generated by incubating 140 μl of the microsomal suspension, 10 μl sinomenine (1 g/l in methanol) (Aldrich, Milwaukee, Wiss.), and 50 μl of the NADPH generating solution under aerobic conditions at 37° C. The incubation was stopped by protein precipitation with 800 μl methanol after 60 minutes for isolation of the metabolites or at other time points for study of time-dependent metabolite formation (see Example 2, below).

After the generation of sinomenine metabolites, HPLC was used to isolate the metabolite of interest. A Bruker LC41D HPLC system equipped with variable wavelength UV detector and autosampler was used (Bruker, Bremen, Germany). HPLC grade solvents were obtained from Baker (Deventer, the Netherlands). To obtain better separation of sinomenine and N-demethyl-sinomenine, two columns were linked in series. Specifically, two 250×10 mm columns filled with Hypersil $C_8$ material (Shandon, Chadwick, UK) of 10 μm particle size and 100 Å pore width (filled by SFD Schambeck, Bad Honnef, Germany) linked in sequence were used.

Samples obtained from the metabolite generation step were centrifuged (2000 g, 2 minutes) and the supernatants were injected into the HPLC system. Sinomenine and its metabolites were isocratically eluted using a 67/33 v/v mobile phase of 50 mM phosphate buffer, pH 5.0, and acetonitrile. The flow rate was 3 ml/min and the UV detection wavelength was 234 nm. Sinomenine and metabolite fractions were manually collected (samples suspected of containing metabolites were collected and tested as described in Example 3, below).

Corresponding isolated fractions from several runs were pooled and evaporated to dryness under reduced pressure over phosphopentoxide. The residues were then reconstituted either in 0.9% NaCl for the biological assays or in methanol for HPLC and mass spectrometry analysis.

Example 2
Time-dependent Study of Sinomenine and N-demethyl Sinomenine

The presence of sinomenine and N-demethyl-sinomenine over time in the presence of microsomes and an NADPH generating solution were determined by HPLC and ultraviolet (UV) analysis.

As described above in Example 1, sinomenine was incubated with human liver microsomes and an NADPH generating system. Samples were removed from the main reaction vessels at five time points, t=0, 15, 30, 60, and 120 minutes, and the reactions were stopped by protein precipitation with methanol. The samples were further prepared for HPLC by centrifugation as described in Example 1.

For the HPLC analysis, a 250×4 mm analytical column was prepared with endcapped $C_{18}$ material of 5 μm particle size. The samples were loaded and isocratically eluted at a flow rate of 1 ml/minute with a 9.0/9.0/12.0/70.0 v/v/v/v solution of methanol/acetonitrile/sodium acetate (0.2 mol/l)/water solution at pH 5.5. Sinomenine and its metabolites were detected with a UV wavelength of 234 nm.

Figure 3:
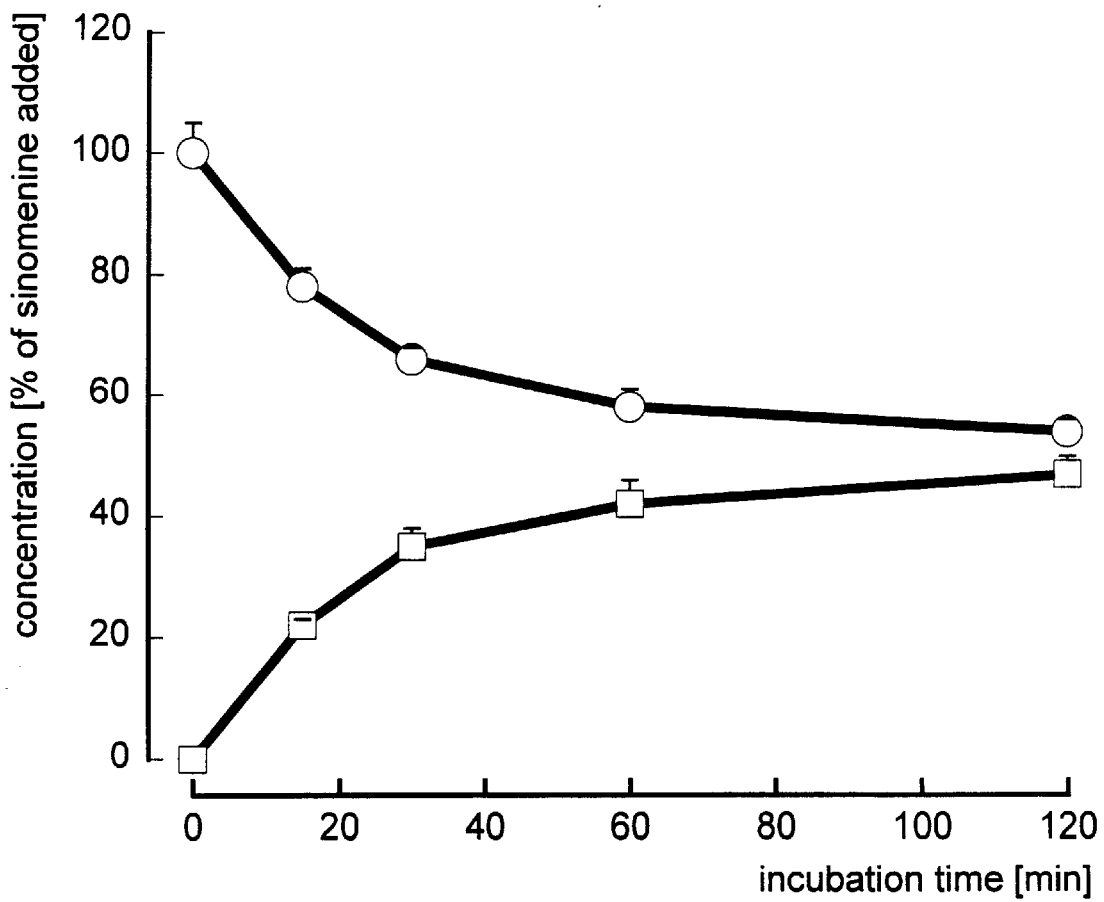
FIG. 3 is a graphical representation of the time-dependent formation of N-demethyl-sinomenine (□) during incubation of sinomenine (○) with human liver microsomes and an NADPH producing system.

The results, presented in FIG. 3, present the mean and standard deviations (partially obscured by data point symbols) for five samples per tested time point. Sinomenine is presented as ○ and its major metabolite, N-demethyl-sinomenine, is presented as □ in FIG. 3. The results present evidence that sinomenine and its major metabolite are present in approximately equal amounts at 120 minutes after the start of the reaction. The experiment was repeated with rat liver microsomes and similar results were obtained.

Example 3
Analytical HPLC

An HPLC system was also used for analysis of the sinomenine metabolism end products. For analytical HPLC, sinomenine and its metabolites were separated on a 250×4 mm LiChroCart column filled with endcapped Supersphere RP-18 material of 5 μm particle size and 100 Å pore width (Merck, Darmstadt, Germany).

The metabolite was prepared as described in Example 1. The samples were centrifuged (2000 g, 2 minutes) and 100 μl of the supernatant was injected into the analytical HPLC system. A control sample was prepared by the method described in Example 1 except that sinomenine and liver microsomes were incubated with an equal amount of phosphate buffer instead of with the NADPH generating solution. An HPLC run of the control sample was also made. The flow rate for the HPLC was set at 1 ml/min and the UV detection wavelength was 234 nm. The analytical column was kept at room temperature.

Sinomenine and its metabolites were isocratically eluted from the column with a mobile phase of 9.0/9.0/12.0/70.0 v/v/v/v methanol/acetonitrile/0.2 M sodium acetate/water, pH 5.5. The various fractions were quantified based on an external sinomenine calibration curve.

Figure 4:
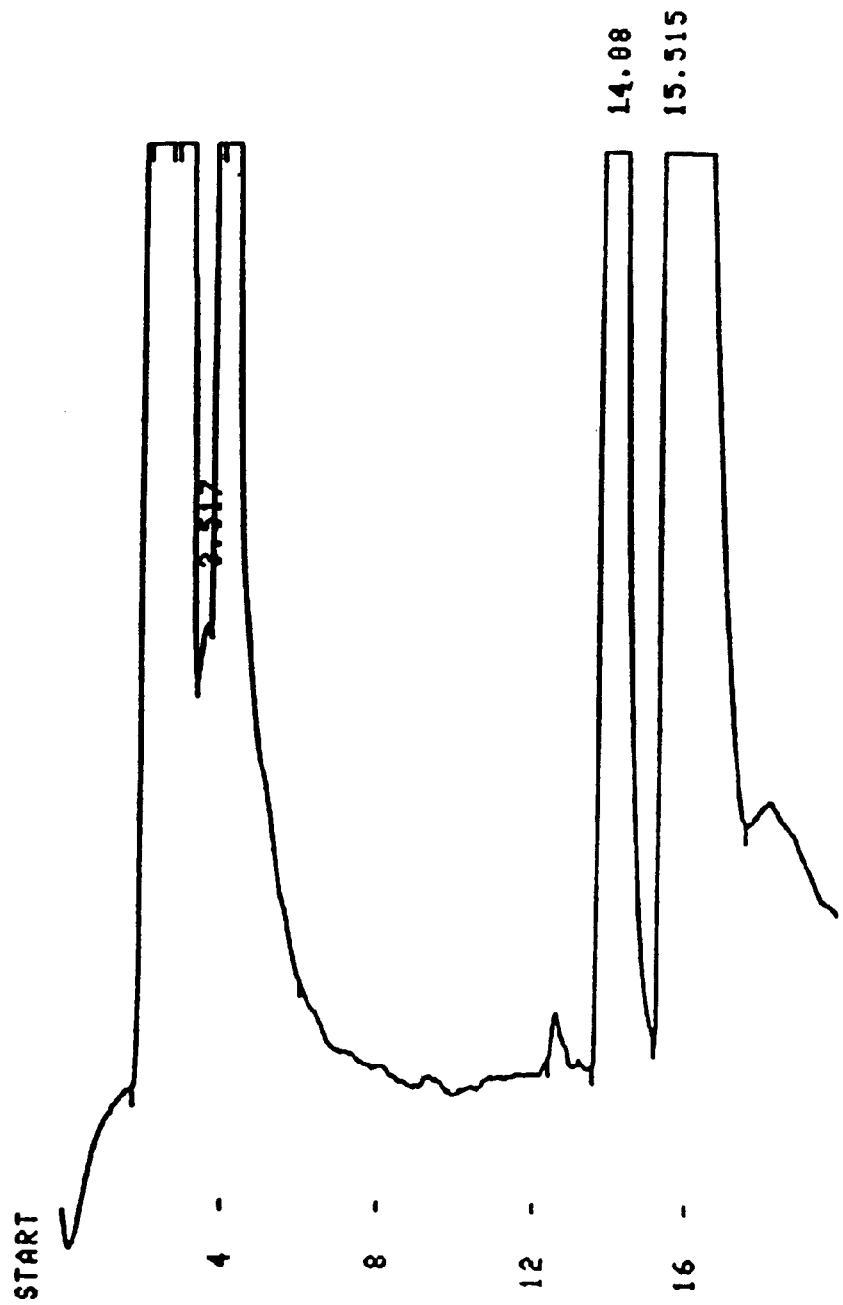
FIG. 4 is an HPLC chromatogram of a sample taken from a rat liver microsomal incubation with sinomenine.

The sinomenine treated with rat liver microsomes and an NADPH generating system as described in Example 1 exhibited, as depicted in FIG. 4, a first peak with a retention time of 14.0–14.5 minutes from time zero in addition to a second peak at approximately 15.5 minutes identified as containing sinomenine. The peak with a retention time of 14.0–14.5 minutes was not present in a run of the control sample. The sample presenting the approximately 14 minute peak was identified as containing sinomenine's major metabolite and was selected for further study.

The shorter retention time of the major metabolite on a lipophilic column, as compared with the sinomenine, provides strong evidence that the metabolite has greater water solubility than the sinomenine.

HPLC chromatograms of samples prepared as above but using human liver microsomes resulted in a similar profile having a peak with a retention time of 14.0–14.5 minutes from time zero and additionally included a second metabolite peak with a shorter retention time than the 14.0–14.5 minute peak having the N-demethyl-sinomenine, and representing less than 10% of the metabolism products formed.

Example 4
Gas Chromatography/Mass Spectrometry Analysis

The structures of sinomenine and of the material eluted at 14.0–14.5 minutes from time zero in Example 2, above, were characterized based on analyses of fragmentation patterns. The major metabolite, eluted at the 14.0–14.5 time point, was thus identified as N-demethyl-sinomenine.

Gas Chromatography (GC) and Mass Spectrometry (MS) in combination with electron impact (EI) ionization was used for structural identification. The GC column portion of the GC/MS system (GC: Carlo Erba 5160, Fisons Instruments, Mainz, Germany; MS: Finnigan-MAT 4515; Finnigan-MAT, Bremen, Germany) was a 300×0.32 cm fused silica column filled with methylsilicone DB-1 (J&F Scientific Products, Cologne, Germany). Helium was used as the GC carrier gas. The injector temperature was 250° C. (split 1/20). The gas chromatography was performed with a temperature program ranging from 100° C.–300° C. with an increase of 6° C. per minute. The EI acceleration voltage was 40 eV and the mass spectra were scanned from m/z= 25–400.

Figure 5:
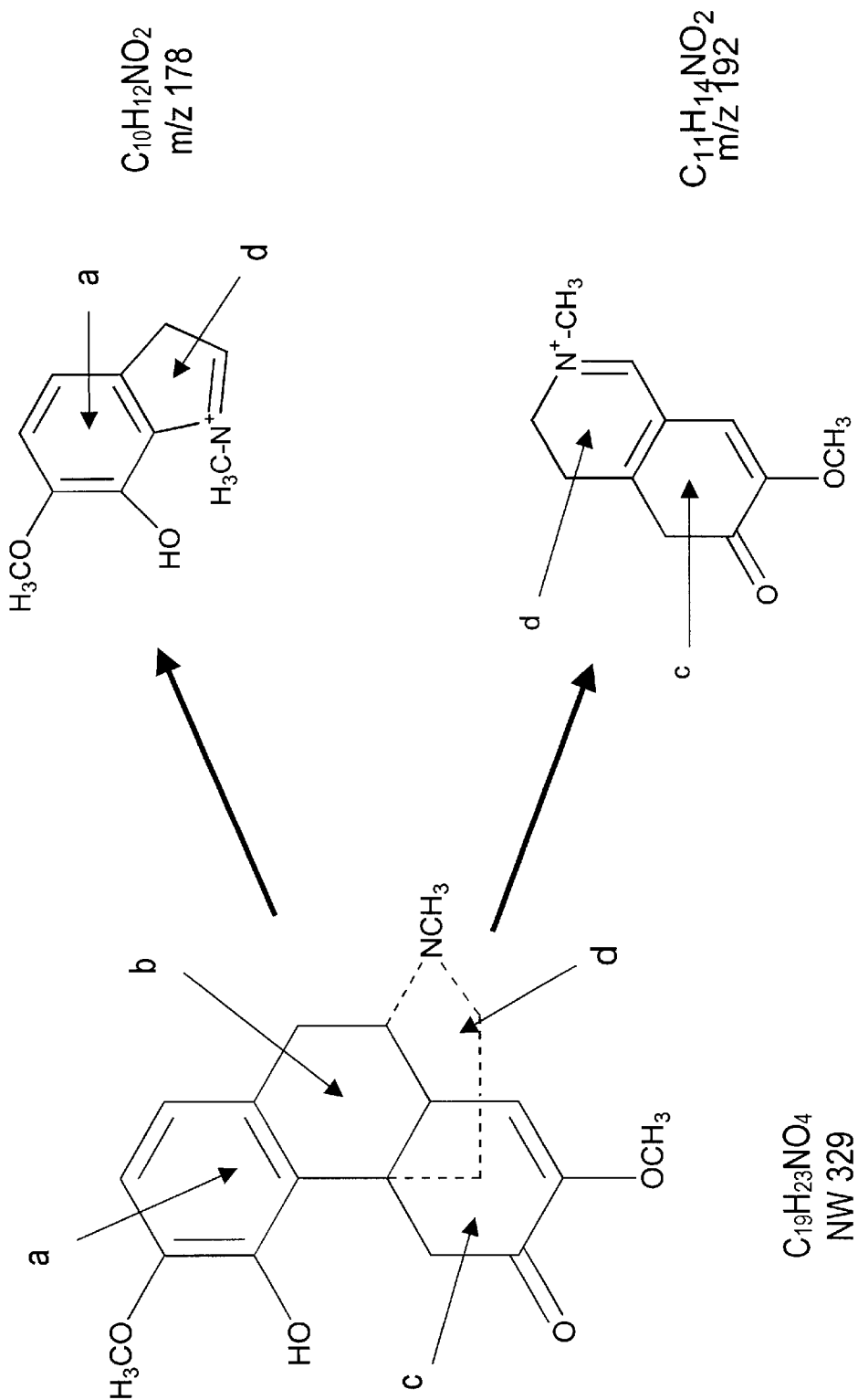
FIG. 5 presents the structures of the major fragments of sinomenine based on electron impact ionization and GC/MS fragmentation analysis.

The structures of sinomenine fragments after electron impact ionization have previously been identified using high resolution mass spectrometry (Audier, H., et al., *Mass Spectrometry of the Morphine Alkaloids, Tetrahydron Letters,* 1:13–22, (1965)) and the accepted structures for the major fragments are depicted in FIG. 5. The four rings of the intact sinomenine molecule ($C_{19}H_{23}NO_4$) are identified by the letters a, b, c, and d. The main fragments of sinomenine are shown in the right-hand portion of FIG. 5 with the letters a, d, and/or c; these letters in the fragments indicate the accepted origins of the rings in the fragment by comparison with the intact sinomenine molecule.

Figure 6A:
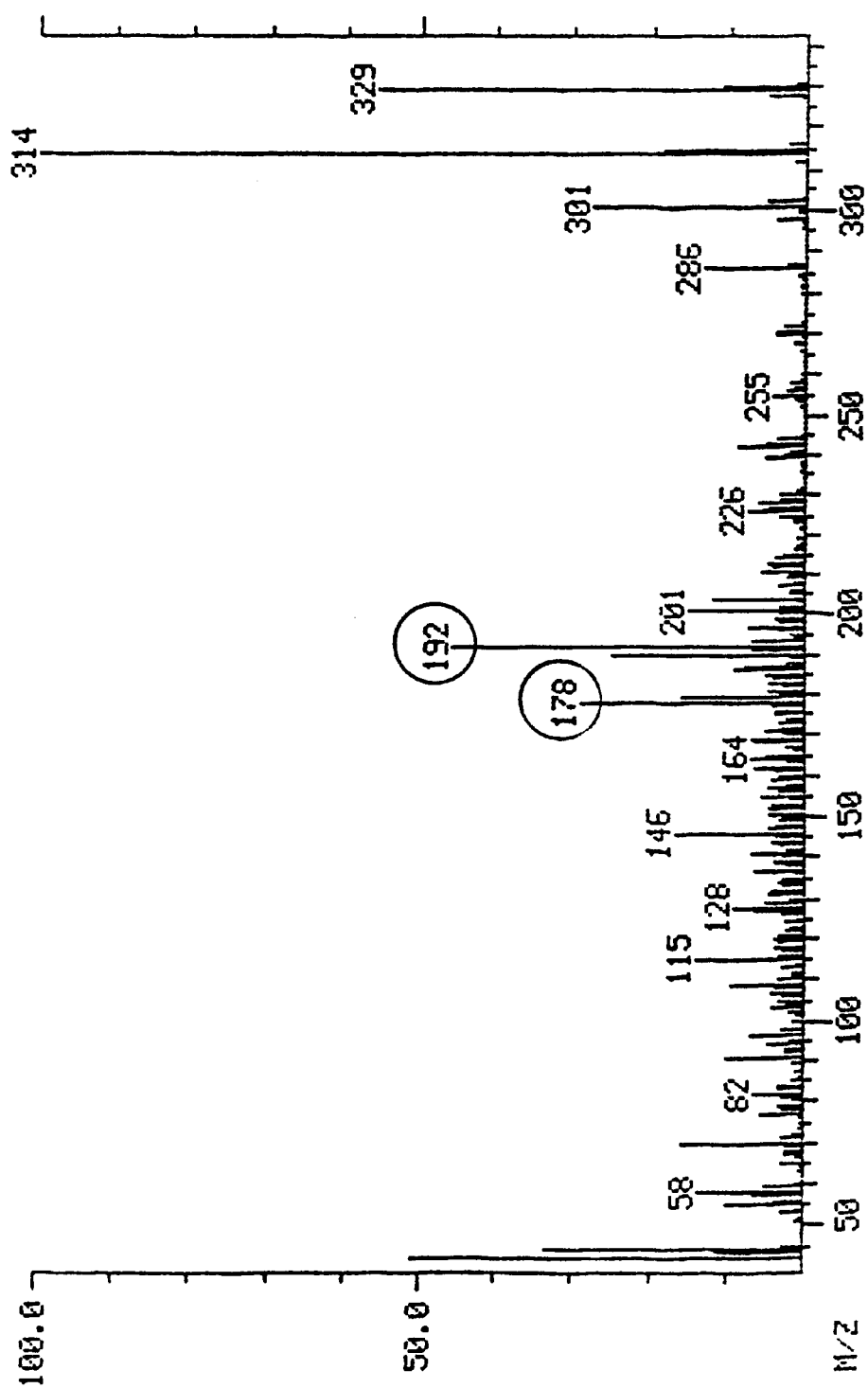
FIGS. 6A–B are the mass spectra for sinomenine (FIG. 6A) and for N-demethyl-sinomenine (FIG. 6B).

The accepted sinomenine fragmentation pattern was confirmed by this experiment. Specifically, for the sinomenine sample, the molecular ion was detected at a mass/charge, or m/z, of 329 (58% of the base peak) with major fragment ions at m/z=192 (47%) and m/z=178 (31%), as illustrated in the mass spectrum of FIG. 6A. The parenthetical numbers (58%, 47%, etc.) given with the descriptions of the fragments indicate the relative height of its peak in the mass spectrum. Peaks representing key fragments which are used for structural identification are marked with circles in FIG. 6A.

Analysis of the isolated metabolite revealed that the molecular ion was at m/z=315 (80%). The difference of the molecular ions of sinomenine and the isolated major metabolite of −14 atomic mass units (amu) (comparison of m/z=329 for sinomenine and m/z=315 for the major metabolite) indicated demethylation in one position.

Figure 2:
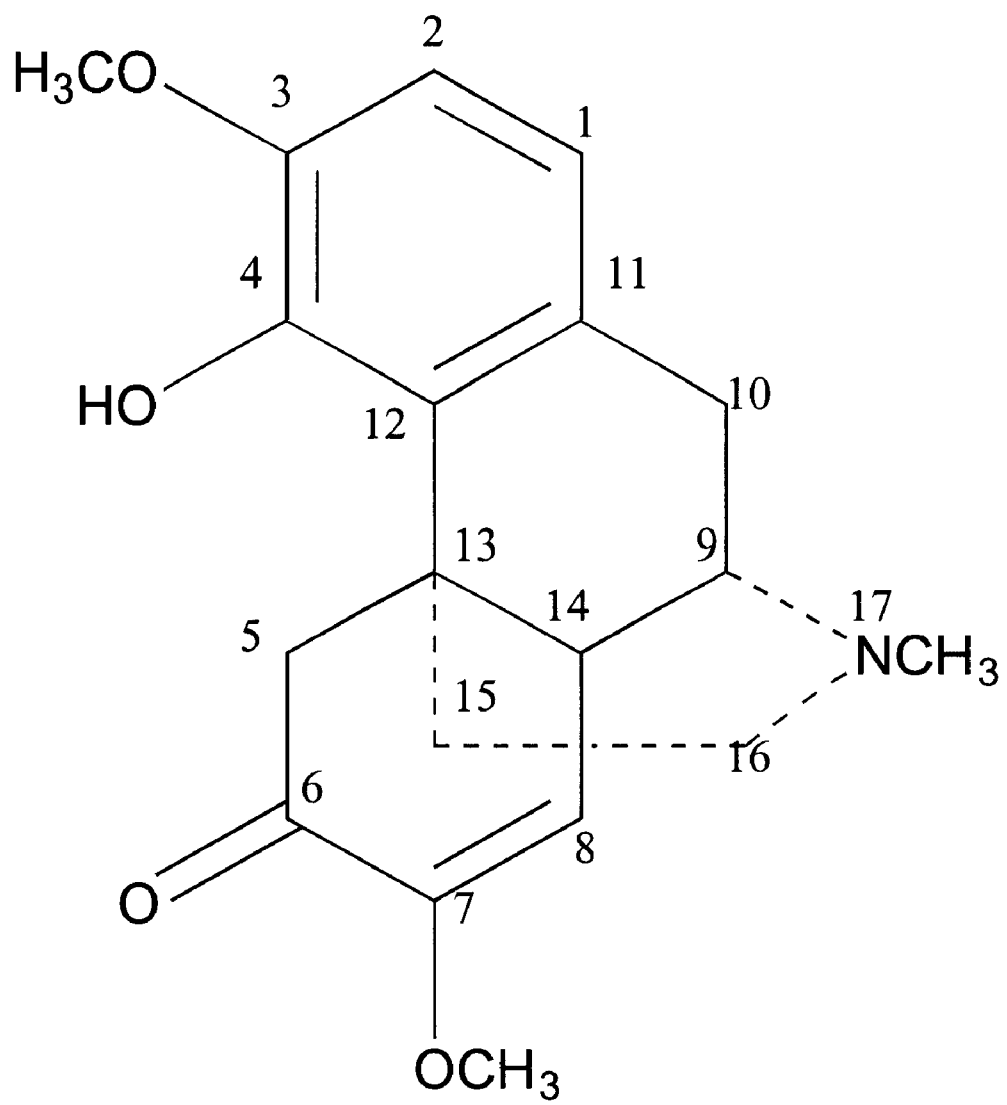
FIG. 2 represents the chemical structure of sinomenine.

With reference to the representation of the sinomenine molecule in FIG. 2, it can be seen that there are three potential demethylation positions in the sinomenine molecule, namely O-demethylation at C(3), O-demethylation at C(7), and N-demethylation. Based on the known fragmentation pattern of sinomenine, the frag mentation pattern expected for the isolated metabolite would be as indicated in Table 1.

TABLE 1

Expected Fragmentation Pattern for Possible Sinomenine Metabolites

| possible metabolite | major fragment ions |
| --- | --- |
| 3-O-demethyl-sinomenine | m/z = 164 and m/z = 192 |
| 7-O-demethyl-sinomenine | m/z = 178 |
| N-demethyl-sinomenine | m/z = 164 and m/z = 178 |

Figure 6B:
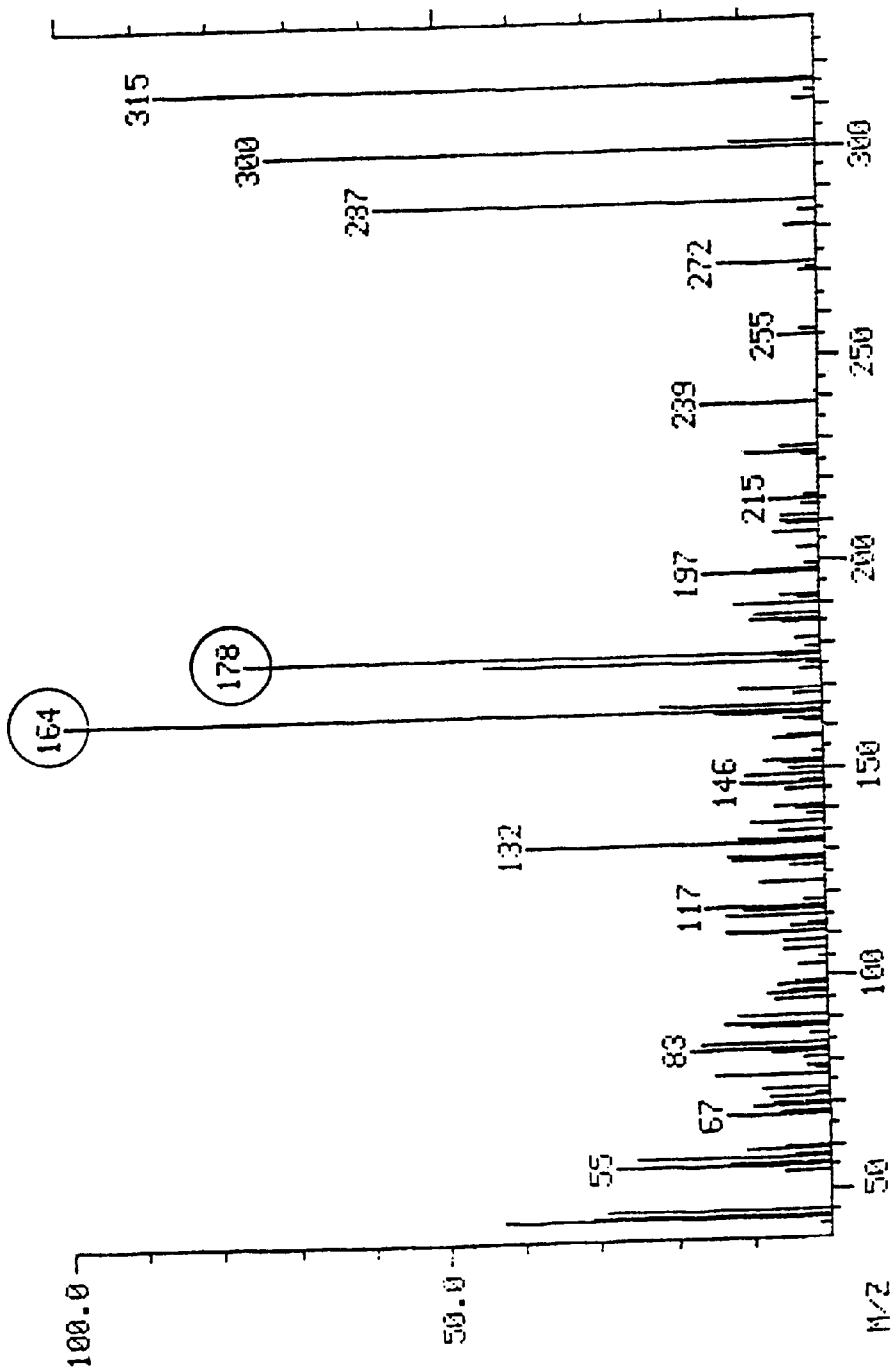
Figure 7:
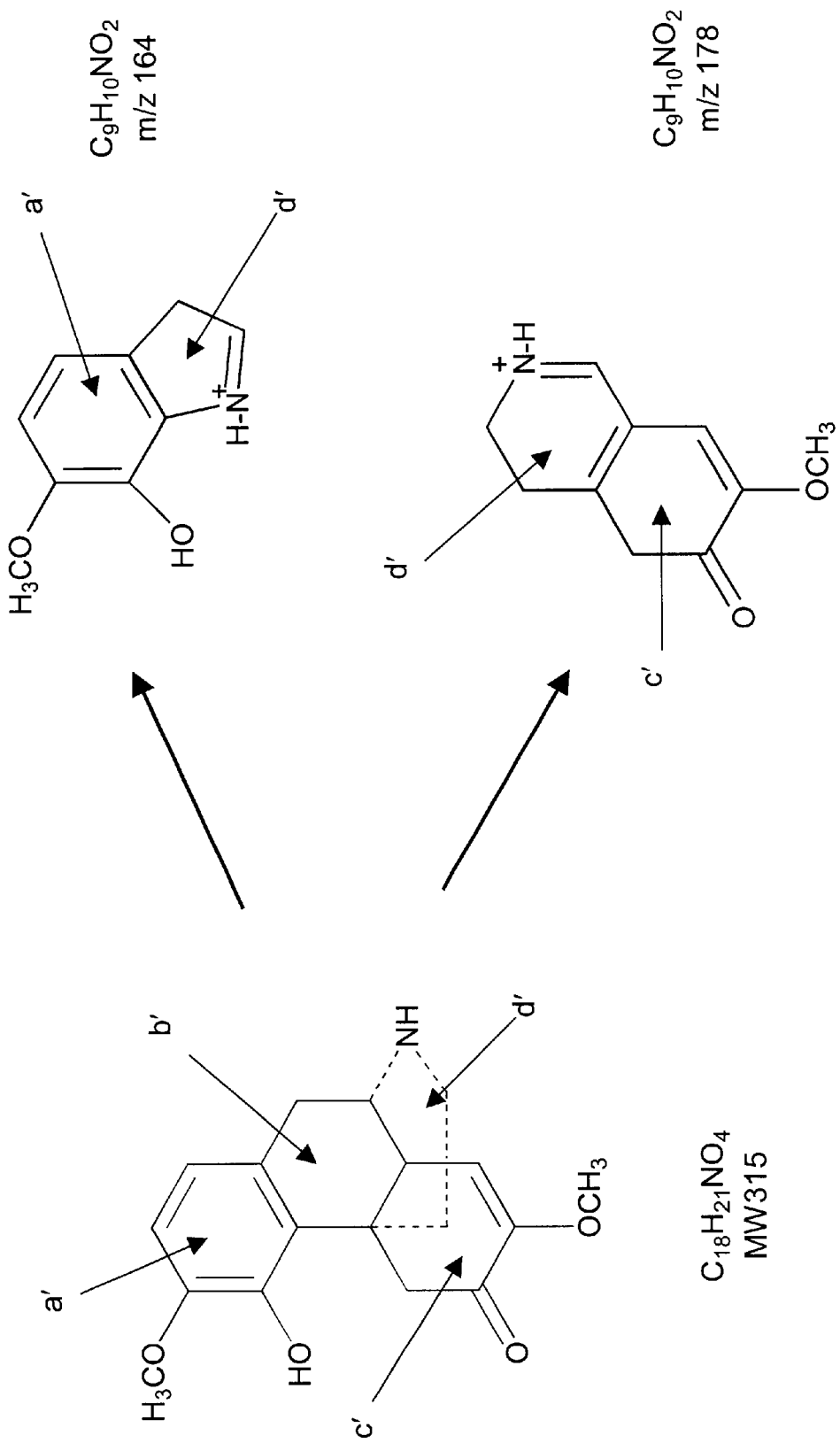
FIG. 7 presents the structures of the major fragments of N-demethyl-sinomenine based on electron impact ionization and GC/MS fragmentation analysis.

The GC/MS and EI analysis of the isolated metabolite indicated major fragment ions at m/z=178 (78%) and m/z=164 (100%), as seen in the mass spectrum of FIG. 6B. As with FIG. 6A, peaks representing key fragments which are used for structural identification are marked with circles in FIG. 6B. This study of the fragmentation pattern for the major metabolite of sinomenine thus indicates that its structure is N-demethyl-sinomenine. The proposed structures for the major fragments are illustrated in FIG. 7. Letters a', b', c', and d' point out rings of the N-demethyl-sinomenine molecule. The rings in the major fragments are labeled with a', d', and/or c', indicating the expected origin by comparison with the intact N-demethyl-sinomenine molecule.

The experimentation in this example was performed with samples generated with rat liver microsomes. The GC/MS and EI analysis results were verified with a sinomenine major metabolite generated by human liver microsomes.

Example 5
Detection of In Vivo Sinomenine Metabolism

N-demethyl-sinomenine was detected as a metabolite in samples obtained from laboratory animals to whom sinomenine was administered.

More particularly, to study its metabolism in vivo, sinomenine was injected intraperitoneally into female Lewis rats at a concentration of 150 mg/kg body weight. Blood was taken after 30 minutes from the rat tail vein and plasma samples were prepared from the blood samples via standard techniques. In a parallel study, MRL-1 pr mice were injected intraperitoneally with either sinomenine at a concentration of 100 mg/kg body weight or physiological saline. Mouse urine was collected over a period of 24 hours.

The collected samples of rat blood and mouse urine from each of these studies were split so that testing could be performed immediately and after storage at −20° C. for one week. HPLC and GC/MS analysis was performed and there were no statistically significant differences in the results obtained from the immediately tested and the frozen samples.

Figure 8:
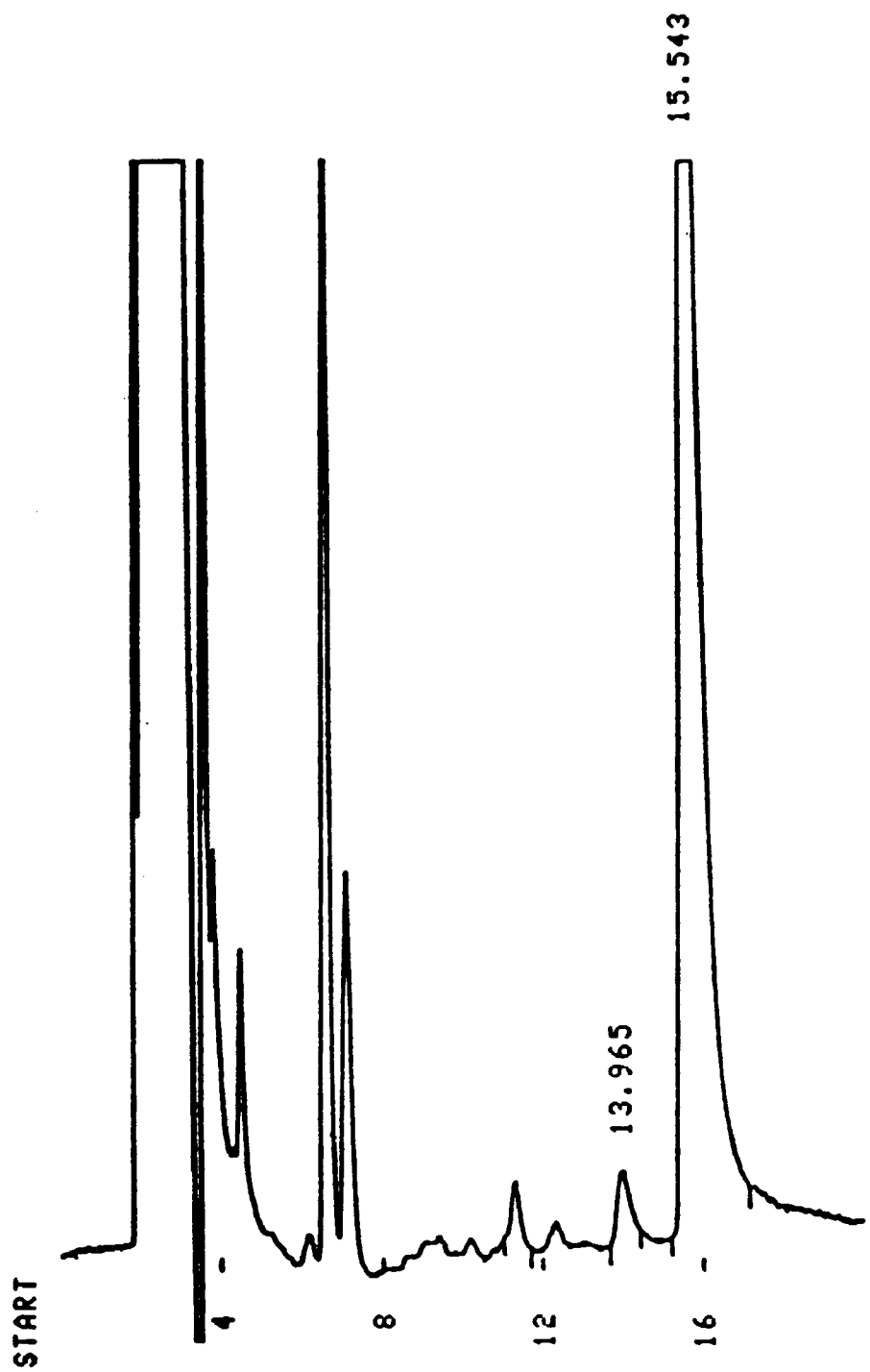
FIG. 8 is an HPLC chromatogram performed on a rat plasma sample obtained from a rat to whom sinomenine was administered.
Figure 9A:
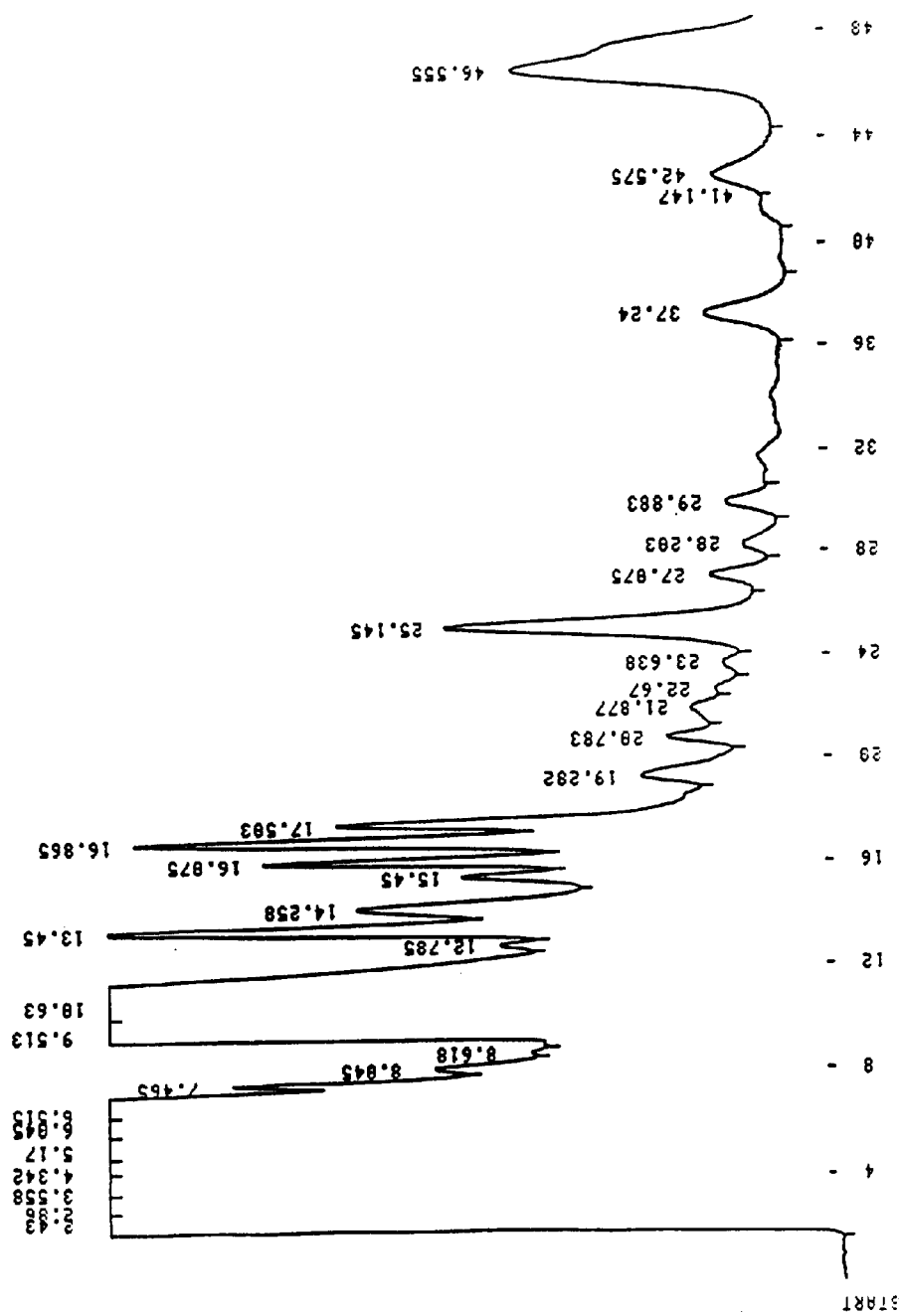
FIGS. 9A–B are HPLC chromatograms of urine samples obtained from mice treated with saline (FIG. 9A) or with sinomenine (FIG. 9B).
Figure 9B:
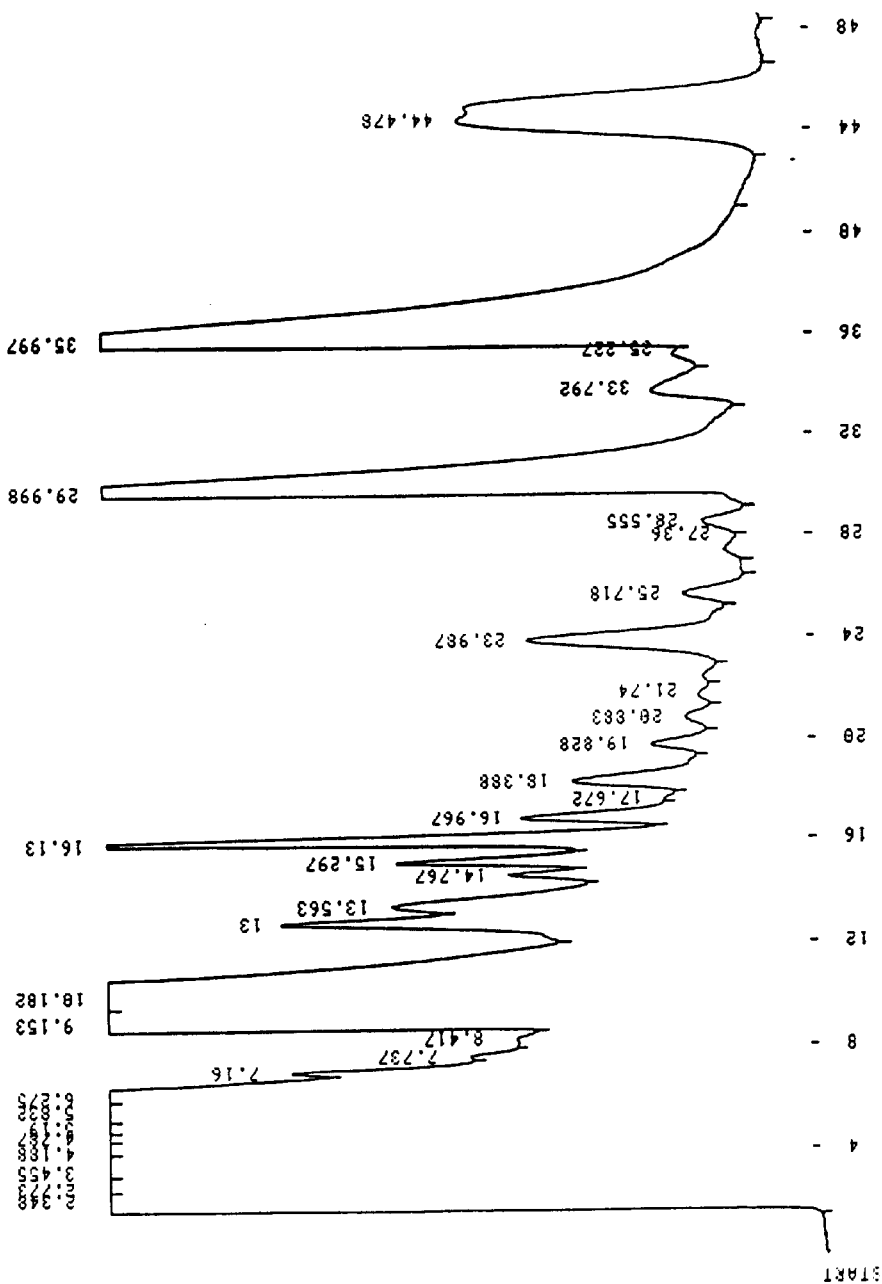

A metabolite peak with the same relative retention time as the major metabolite isolated after incubation of sinomenine and NADPH generating solution with rat microsomes or human liver microsomes was obtained upon analysis of the rat blood and mouse urine samples. Specifically, FIG. 8 is an HPLC chromatogram performed on a representative plasma sample obtained from the rat study, and it shows both a sinomenine peak at approximately 15.5 minutes and a smaller peak with a shorter retention time, representing N-demethyl-sinomenine, at approximately 14 minutes from time zero. FIGS. 9A–B show HPLC chromatograms run on urine samples obtained from mice treated with saline (FIG. 9A) or with sinomenine (FIG. 9B). Sinomenine elution occurred at approximately 36 minutes and N-demethyl-sinomenine elution occurred at approximately 30 minutes, as seen in FIG. 9B. The identifications of sinomenine and its major metabolite present in the samples obtained from these studies were confirmed through HPLC and GC/MS examination as described in Examples 3 and 4.

Example 6

Biological Activity of N-demethyl-sinomenine

In an OKT3-stimulated human peripheral blood mononuclear cell assay, the relative biological activities of sinomenine and N-demethyl-sinomenine were tested. N-demethyl-sinomenine inhibited interleukin-2 (IL-2) synthesis with a half-maximal inhibition concentration ($IC_{50}$) that indicated superior biological activity, approximately five times greater, over that of simonenine in the same assay.

The OKT3-stimulated human peripheral blood mononuclear cell assay was performed as described in Liu, L. et al., *Inhibition of Lymphocyte Proliferation by the Anti-Arthritic Drug Sinomenine*, Int. J. Immunopharmac., 16(8):685–691, (1994). Human Peripheral Blood Mononuclear Cells (PBMCS) were isolated from heparinized blood drawn from healthy adults. After separation from other blood components by density gradient centrifugation on Ficoll-hypaque (Biochrom, Berlin, Germany), the PBMCs were suspended in RPMI 1640 medium/10%FCS (RPMI 1640 medium with L-glutamine and nonessential amino acids: Gibco (Eggenstein, Germany); fetal calf serum (FCS): PAA Biologics (Marburg, Germany)).

The PBMCs ($10^5$ cells in a total volume of 150 μl per well) were activated by incubation with the monoclonal anti-T-cell receptor/CD3 complex antibody OKT3 (1 μg/l) for 14 hours. During this incubation, either sinomenine or N-demethyl-sinomenine was present in each of the main experimental wells at concentrations ranging from $10^{-8}$ to $10^{-3}$ M, as indicated on the x-axes of the graphs of FIGS. 10A and 10B. Control wells containing neither sinomenine nor its major metabolite were also prepared. The concentration of secreted IL-2 in the supernatants of activated PBMCs was determined using a commercial ELISA kit (Immunotech, Hamburg, Germany) following the manufacturer's instructions. In each of FIGS. 10A–B, the mean and standard error of three independent experiments are shown.

Figure 10A:
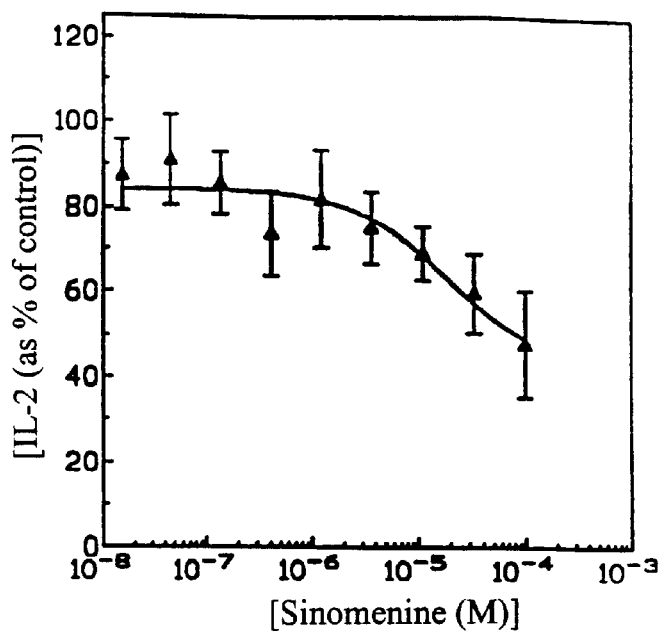
FIGS. 10A–B are graphs representing IL-2 inhibition by sinomenine (FIG. 10A) or by N-demethyl-sinomenine (FIG. 10B) in an OKT3-stimulated PBMC assay.
Figure 10B:
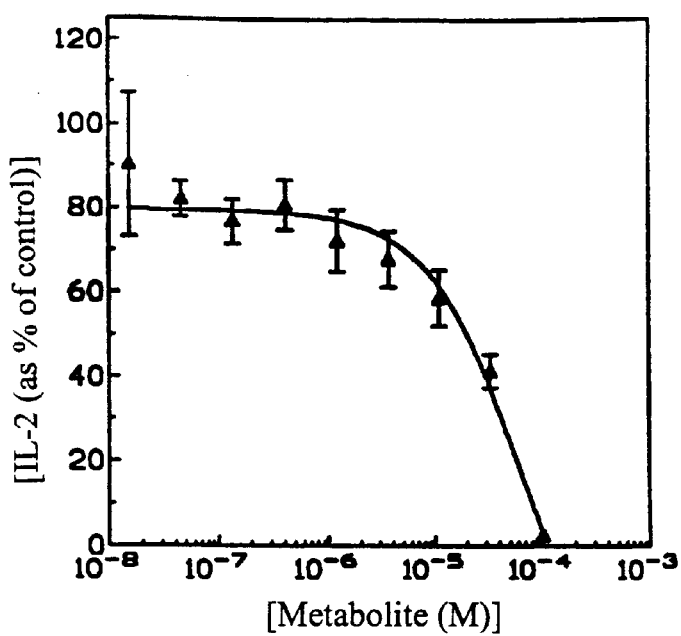

FIG. 10A presents the results for inhibition of IL-2 secretion by sinomenine. The concentration of IL-2 production, as a percentage of the control (100% equalled 1135 pg/ml, in this instance), was plotted against the molar concentration of sinomenine for each data point. The curves depicted were generated by a curve fit computer program (Microcal Origin Version 3.5). As generated by the curve fit program and evidenced in FIG. 10A, sinomenine inhibited IL-2 synthesis with an $IC_{50}$ of 100 μmol/l in the OKT3-stimulated PBMC assay. FIG. 10B presents the results for N-demethyl sinomenine. The N-demethyl-sinomenine exhibited an $IC_{50}$ of 20 μmol/l in the assay, as presented by the curve fit program and evidenced in the figure. This example illustrates the significantly greater immunosuppressive and anti-inflammatory activity possessed by N-demethyl-sinomenine relative to sinomenine.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A compound having the following formula:

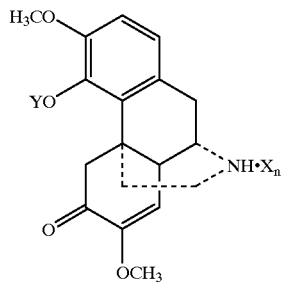

wherein there is an optional substitution at $X_n$ to make a pharmaceutically acceptable salt or hydrate of the compound and further wherein Y is H or there is a substitution at Y to make a pharmaceutically acceptable salt or ester of the compound.

2. A pharmaceutically acceptable salt or hydrate of the compound of claim 1, wherein n is a number from 1–5 and X is $H_2O$ or is derived from the group consisting of hydrochloric acid, hydrobromic acid, sulfuric acid, nitric acid, phosphoric acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid.

3. A pharmaceutically acceptable salt of the compound of claim 1, wherein Y is selected from the group consisting of sodium, potassium, lithium, ammonium, calcium, and magnesium.

4. A pharmaceutically acceptable ester of the compound of claim 1, wherein YO is selected from the group consisting of esters of alkanoic acids, alkenoic acids, alkynoic acids, and benzoic or other aromatic acids.

5. A pharmaceutical composition comprising the compound of claim 1, and a pharmaceutically acceptable carrier.

6. A method of treating a disorder, the method comprising:

administering to a patient a therapeutically effective amount of the pharmaceutical composition of claim 5.

7. The method of claim 6 wherein the disorder is selected from the group consisting of rheumatoid arthritis, neuralgia, ankylosing spondylitis, Reiter's syndrome, Behcet's syndrome, lupus erythematosus, nephritis, psoriasis, multiple sclerosis, hepatitis, vasculitis syndroms, atherosclerosis, and bronchiolitis obliterans.

8. A method of preventing the rejection of transplanted organs or cells in a patient, comprising administering to the patient a therapeutically effective amount of the pharmaceutical composition of claim 5.

9. A compound having the following formula:

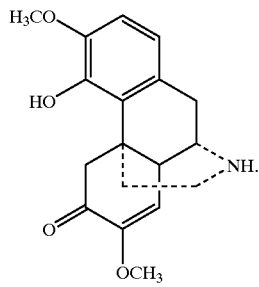

10. A pharmaceutical composition comprising:
(a) a compound having the following formula:

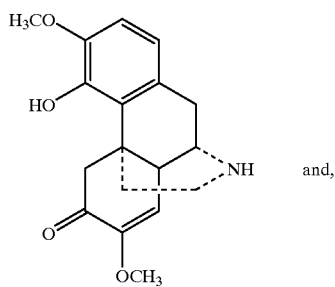

and, (b) a pharmaceutically acceptable carrier.

11. A method of treating a disorder, the method comprising:
administering to a patient a therapeutically effective amount of the pharmaceutical composition of claim 10.

12. The method of claim 11 wherein the disorder is selected from the group consisting of rheumatic diseases, autoimmune diseases, and inflammatory degeneration.

13. The method of claim 11 wherein the disorder is selected from the group consisting of rheumatoid arthritis, neuralgia, ankylosing spondylitis, Reiter's syndrome, Behcet's syndrome, lupus erythematosus, nephritis, psoriasis, multiple sclerosis, hepatitis, vasculitis syndroms, atherosclerosis, and bronchiolitis obliterans.

14. A method of preventing the rejection of transplanted organs or cells in a patient, comprising administering to the patient a therapeutically effective amount of the pharmaceutical composition of claim 10.

15. A method of treating a patient in need of an immunosuppressive, anti-inflammatory, or analgesic agent, the method comprising a administering to the patient a therapeutically effective amount of the pharmaceutical composition of claim 10.

16. A metabolite of sinomenine having greater water solubility than sinomenine as evidenced by lipophilic reversed phase HPLC column.

17. A metabolite of sinomenine, wherein said metabolite has a first retention time on a lipophilic reversed phase HPLC column, said sinomenine has a second retention time on said lipophilic reversed phase HPLC column, and said first retention time is shorter than said second retention time.

18. A metabolite of sinomenine having greater biological activity than sinomenine as evidenced by OKT3-stimulated human peripheral blood mononuclear cell assay.

* * * * *